United States Patent [19]
Malawer et al.

[11] Patent Number: 6,011,160
[45] Date of Patent: Jan. 4, 2000

[54] CROSSLINKED POLYVINYLPYRROLIDONE (PVPP) COPOLYMER OF VINYL PYRROLIDONE (VP) AND MONOMER DERIVED FROM 1-VINYL-3-(E)-ETHYLIDENE PYRROLIDONE (EVP)

[75] Inventors: Edward G. Malawer, Wayne, N.J.; Victor Kabanov, Moscow, Russian Federation; Kolazi S. Narayanan, Wayne; Michael A. Tallon, Aberdeen, both of N.J.; Susan Y. Tseng, Staten Island, N.Y.; Philip F. Wolf, Bridgewater, N.J.

[73] Assignee: ISP Investments Inc., Wilmington, Del.

[21] Appl. No.: 08/932,893

[22] Filed: Sep. 18, 1997

[51] Int. Cl.[7] .................... G07D 207/09; G07D 207/12
[52] U.S. Cl. .................... 548/543; 548/550; 546/177; 526/263
[58] Field of Search ............... 526/263; 548/569, 548/550, 543; 546/177

[56] References Cited

PUBLICATIONS

Howard et al., "4–Substituted–2, 3, 5–pyrrolidinetriones," J. Am. Chem. Soc., vol. 80, pp. 3924–3928, 1958.

*Primary Examiner*—Johann Richter
*Assistant Examiner*—Jane C. Osowecki
*Attorney, Agent, or Firm*—Walter Katz; William J. Davis; Marilyn J. Maue

[57] ABSTRACT

What is described herein is a crosslinked polyvinylpyrrolidone (PVPP) copolymer of vinyl pyrrolidone (VP) and monomer derived from 1-vinyl-3-(E)-ethylidene pyrrolidone (EVP).

16 Claims, No Drawings

CROSSLINKED POLYVINYLPYRROLIDONE (PVPP) COPOLYMER OF VINYL PYRROLIDONE (VP) AND MONOMER DERIVED FROM 1-VINYL-3-(E)-ETHYLIDENE PYRROLIDONE (EVP)

BACKGROUND OF THE INVENTION

1. Field of the Invention

This invention relates to crosslinked polymers of vinyl pyrrolidone, and, more particularly, to crosslinked copolymers of vinyl pyrrolidone and a monomer derived from 1-vinyl-3-(E)-ethylidene pyrrolidone (EVP).

2. Description of the Prior Art

Crosslinked polyvinylpolypyrrolidone (PVPP) is widely employed as a clarifying agent in the industrial purification of wine and beer solutions, particularly for the removal by adsorption of organic impurities such as polyphenols, tannins and anthrocyanins which may be present in the aqueous solution. However, this polymer is incapable of removing heavy metal ions, in particular, copper and iron ions, which also contribute to the toxicity and cloudiness of such solutions.

PVPP is made by popcorn or proliferous polymerization of vinyl pyrrolidone (VP) in the presence or absence of added crosslinking agents, as described in U.S. Pat. Nos. 3,277,066; 3,306,888; 3,759,880; 3,933,766; 3,992,562; and 5,391,668, and by F. Haaf et al. in Polymer J. 1701), p. 143–152 (1985), entitled "Polymer of N-Vinyl Pyrrolidone: Synthesis, Characterization and Uses".

Controlled modification of the properties of PVPP may be accomplished by the introduction of comonomers with vinyl pyrrolidone which contain functional or ligand groups capable of preferential binding of copper or iron ions. For example, U.S. Pat. No. 5,094,867 described a copolymer of vinyl pyrrolidone containing 50–99.5% of a ligand-containing comonomer, particularly N-vinyl imidazole, (NVI), which is an amine-containing comonomer, to remove such heavy metal ions. However, the NVI comonomer in this system must be used in very high concentrations to achieve the desired binding effect. In addition, the vinyl pyrrolidone content of this copolymer is much less than for PVPP alone, which reduces the useful properties of the copolymer as a clarifying agent.

Accordingly, it is an object of the present invention to provide a new and improved PVPP copolymer for use in the industrial clarification of aqueous solutions.

Another object herein is to provide a crosslinked PVPP copolymer which includes a heavy metal chelating comonomer for vinyl pyrrolidone, which comonomer is present in small amounts but is effective in completing and removing traces of heavy metals such as copper and iron ions present in aqueous solutions.

A particular object herein is the provision of a vinyl pyrrolidone copolymer which contains a monomer derived from 1-vinyl-3-(E)-ethylidene pyrrolidone (EVP).

Still another object herein is to provide a vinyl pyrrolidone copolymer which contains 3-(2-aminoethyl)-α-aminoethyl-N-vinyl pyrrolidone (AEAEVP) as comonomer therein.

A further object herein is to provide a proliferous polymerization process for making such copolymers.

These and other objects and features of the invention will be made apparent from the following more particular description of the invention.

SUMMARY OF THE INVENTION

A crosslinked PVPP copolymer is provided herein which contains predominately vinyl pyrrolidone (VP) monomer, and, in small amounts, a heavy metal chelating comonomer derived from 1-vinyl-3-(E)-ethylidene pyrrolidone (EVP) having the formula:

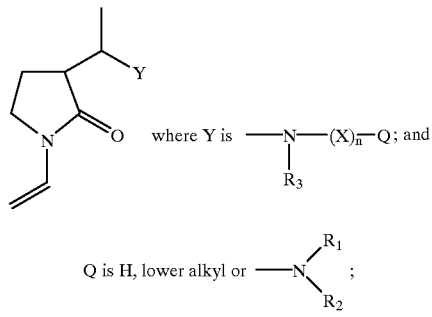

where Y is $-\text{N}(R_3)-(X)_n-Q$; and

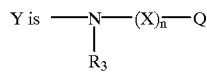

$Q$ is $H$, lower alkyl or $-N(R_1)(R_2)$;

where;

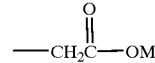

$Y$ is $-\text{N}(R_3)-(X)_n-Q$ and $R_1$, $R_2$ and $R_3$ are independently H, lower alkyl, alkylene carboxylate, alkylene phosphonate or alkylene sulfonate, or 2-ethyl (3-N-vinyl pyrrolidonyl);

$X$ is alkylene, arylene, cycloalkylene or a heterocylic metal chelating group, and $n$ is 1–10.

Preferably, $R_3$ is H and $R_1$ and/or $R_2$ is $$-CH_2\overset{O}{\underset{\|}{C}}-OM$$

where

M is H or monovalent alkali metal; an n is 1–6.

A typical derivatized EVP for use as a comonomer for polymerization with VP is 3-(2-aminoethyl)-α-aminoethyl-N-vinyl pyrrolidone (AEAEVP).

A typical crosslinked PVPP copolymer of the invention comprises, by weight, about 80–90% VP, about 5–15% AEAEVP and about 1–5% EVP.

DETAILED DESCRIPTION OF THE INVENTION

In accordance with the invention, a new and improved crosslinked polyvinylpclypyrrolidone (PVPP) copolymer is provided herein which contains a comonomer in small amounts which can effectively chelate with and remove traces of copper and iron cations present in aqueous solutions.

A suitable comonomer is 3-(2-aminoethyl)-α-aminoethyl-N-vinyl pyrrolidone (AEAEVP), which is made by a Michael addition reaction between one mole of 1-vinyl-3-(E)-ethylidene pyrrolidone (EVP) (U.S. Pat. No. 5,391,668) and one mole of ethylenediamine (EDA). The comonomer may be generated in situ during the course of proliferous polymerization of vinyl pyrrolidone, or obtained independently of the polymerization, and added to the vinyl pyrrolidone monomer to form the polymerization reaction mixture. Excess EVP present in the reaction product of the Michael addition reaction may be used as the crosslinker in the polymerization process. The Michael addition reaction proceeds as follows:

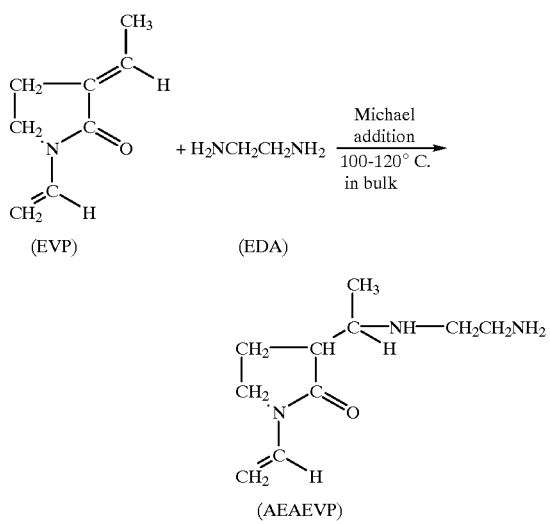

The EVP reactant is a white, needle-shaped crystalline solid having a melting point of 59–61° C.

The AEAEVP monomer also may be generated in situ from a polymerization charge of EVP and EDA, and VP. Similarly, EVP itself may be generated in situ from the VP reactant, as described in U.S. Pat. No. 5,391,668.

While the use of EDA as a reactant is used to illustrate the formation of a suitable monomer for proliferous polymerization with VP and EVP, it will be understood that the equivalents of EDA may be used as well. For example, diethylene triamine (DETA), triethylenetetramine (TETA), etc. may be used in place of EDA, as illustrated in the following examples. Similarly, alkylene-substituted amines including such substituents with aryl, cycloalkyl or alkylene carboxylic groups may be considered equivalents of EDA. Those groups which enhanced the overall chelation abilities of the resultant polymer are considered as preferred equivalents of the simple EDA. Such materials can operate at an acid pH which may be desirable in beer and wine clarification processes.

The invention will now be described in more detail in the following examples.

Examples 1–2
Preparation of AEAEVP Monomer (EVP/EDA -1:1 Mole Ratio)

Example 1

25 g of EVP (MW 137) and 10.95 g of EDA (MW 60) were charged into a 150 ml pressure vessel, and, after a nitrogen purge, was sealed at 110° C. and allowed to react overnight. The contents then were analyzed by GC measurements. The results are shown in Table 1 below.

TABLE 1

| Time (hrs) | Wt. % EVP | Wt. % EDA |
|---|---|---|
| 0 | 69.54 | 30.46 |
| 16 | 13.75* | 7.73* |
| Wt. % Reacted | 55.79% | 22.73% |

Mole ratio of EVP/EDA reacted: (55.79/137)/22.73/60 = 1.07.
*GC/MS analysis of the reaction product indicated the presence of the desired AEAEVP monomer. The proton ($^1$H) and $^{13}$C NMR spectral data was consistent with a 1:1 addition product.

TEST PROCEDURE
* GC Method:
  % EVP remaining in the mixture was calculated using 2-dodecanol as an internal standard; and
  % EDA remaining was calculated using several concentrations of EDA as an external standard.

Example 2

14.251 g of EVP was charged into a 150 ml pressure vessel equipped with a 2-hole metal plate. The system was purged with nitrogen for 30 minutes using 2 syringe needles, one for the $N_2$ purge and the other to relieve the air pressure in the bottle. Then 6.37 g of EDA was added by means of a syringe needle while opening the other hole to relieve the air pressure. Then the contents were heated to 100° C. under reflux while stirring magnetically. After about 12 hours cessation of reflux of the high vapor pressure reactants was observed, which was an indication of formation of the reaction product and of completion of the reaction. The reaction vessel then was cooled to room temperature. The product was a clear, yellow liquid containing AEAEVP monomer.

Example 3

A 150 ml pressure bottle equipped with a magnetic stirrer was charged with 30 g of EVP and sealed with a two-hole rubber gasket metal cap. Nitrogen was purged through the bottle using a 12 inch syringe needle for half an hour. Using a 50 ml syringe, 72.26 g of ethylene diamine (EDA) was introduced into the pressure bottle, and at the same time, the nitrogen purge was disconnected. The reaction bottle then was placed in an oil bath at 110° C. and held there for 16–24 hours with constant stirring. Then the reaction bottle was cooled to room temperature and discharged. The AEAEVP monomer was formed in excess EDA. Residual EVP in the solution mixture was determined by GC as being <1%.

Thereafter excess EDA was stripped off by vacuum distillation (<0.5 mm Hg) at a temperature below 50° C. The AEAEVP monomer obtained had a purity in excess of 97%; its chemical structure was confirmed by GC/MS, $^1$H and $^{13}$C NMR analysis.

Examples 4–5
Proliferous Polymerization of VP/EVP/AEAEVP Reaction Mixtures

Example 4

The reaction product of Example 1 (12.27 g), which contained 1.35% EVP and 8–9% AEAEVP, and 112.73 g VP (89%), in 31.25 g distilled water, were heated to 120° C. in a Büchi reactor, held at that temperature for 2 hours, and then cooled to 100° C., at which temperature proliferous polymerization occurred over a period of one hour. The resultant product was the desired crosslinked copolymer of VP and AEAEVP including EVP as crosslinker in proportions of the starting reactants.

Example 5

The reaction product (20.27 g) of the Michael addition of 30 g of EVP and 13.14 g of EDA having a 1:10 ratio of EVP/EDA, and containing 2.2% EVP and 14% AEAEVP, with 104.73 g of VP, and 31.25 g of water were heated in a Büchi reactor to 100° C. A proliferous polymerization reaction then took place over a period of one hour. A similar copolymer product as in Example 4 was obtained.

Example 6

Proliferous Polymerization of Diethylenetriamine (DETA) with EVP Reactant: 1:1 mole ratio of EVP/DETA 10 g of EVP were charged into a 150 ml reaction vessel and purged with nitrogen. Then 7.52 g of DETA were introduced and the reactants were heated at 110° C. for 16 hrs. The reaction proceeded as follows:

| Time | Wt. % EVP | Wt. % DETA (MW 103) |
|---|---|---|
| Start | 57.08% | 42.92% |
| 16 Hrs. | 10.13% | 12.00% |
| Wt. % reacted | 46.95% | 30.92% |

Mole Ratio of EVP/EDA Reacted: (46.95/137):(30.92/103) = 1.14

| Popcorn Copolymer of the reaction products: | |
|---|---|
| 2.2% EVP | 16.0 grams of the above reactant |
| 83.78% VP | 107.87 grams of VP monomer |
| approx. 14% comonomer | 31.25 grams of distilled water |
| | 1.1292 grams of EVP crystals |
| | Heated in Bucchi reactor to |
| | 100° C. for proliferous |
| | polymerization. |

The product is a white slurry; the first washing of the mother liquid contains the unreacted VP and EVP-adduct comonomer.

Example 7

Proliferous Polymerization of Triethylenetetramine (TETA) with EVP Reactant: 1:1 mole ratio of EVP/TETA 10 g of EVP in 150 ml reaction bottle, nitrogen purged, then introduced 10.66 g of TETA (60%) and heated at 110° C. for 15 hrs.

| Time | Wt. % EVP | Wt. % TETA (MW 146) |
|---|---|---|
| Start | 48.38% | 51.67% |
| 15 Hrs. | 17.93% | 27.85% |
| Wt. % reacted | 30.50% | 23.75% |

Mole Ratio of EVP/EDA Reacted: (30.50/137):(23.75/146) = 1.37

| Popcorn Copolymer of the reaction products: | |
|---|---|
| 2.2% EVP | 15.0 grams of the above reactant |
| 88% VP | 110.0 grams of VP monomer |
| approx. 9% comonomer | 31.25 grams of distilled water |
| | Heated in Bucchi reactor to |
| | 100° C. for proliferous |
| | polymerization. |

Reaction is fast. The product is white solid.

Example 8

Dimethylethylenediamine (DMEDA) with EVP Reactant: 1:1 mole ratio of EVP/DMEDA 10 g of EVP (Mwt. 137) in 6.42 gm of DMEDA (Mwt. 88) in 150 ml of pressure bottle. (Nitrogen purged, 110° C. overnight).

| Time | Wt. % EVP | Wt. % (DMEDA) |
|---|---|---|
| To | 60.90% | 39.10% |
| T24 | 29.78% | 20.62% |
| Wt. % reacted | 31.12% | 18.48% |

Mole Ratio of EVP/DMEDA Reacted: (31.12/137):(18.48/88) = 1.08

The product is mainly DMAEAEVP monomer. Its chemical structure is confirmed by GC/MS.

Example 9

(Copper Removal by Polymers)

The crosslinked polymer of Example 4 was introduced separately at 5 g/l into 5, 10 and 20 ppm aqueous $Cu^{++}$ solutions of copper sulfate and pentahydrate. The mixture was stirred for a total contact time of 20 minutes. An aliquot of each solution was withdrawn and passed through a glass fiber filter to remove any adhering polymer. The aliquot then was analyzed for residual copper ions by atomic absorption spectroscopy. The percent copper removal was calculated by subtraction of the final copper concentration from the initial copper concentration. A total of 94% Cu was removed from the 5 ppm solution, 94% Cu was removed from the 10 ppm solution, and 79% Cu was removed from 20 ppm solution.

While the invention has been described with particular reference to certain embodiments thereof, it will be understood that changes and modifications may be made which are within the skill of the art. Accordingly, it is intended to be bound only by the following claims, in which:

What is claimed is:

1. A monomer having the formula:

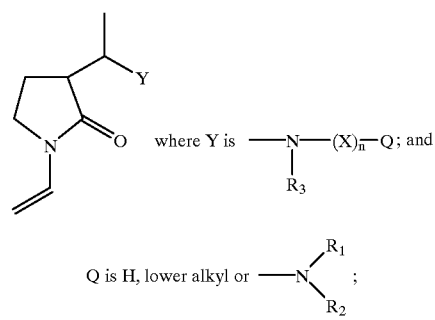

where Y is $-\!\!-\!\!N(R_3)\!\!-\!\!(X)_n\!\!-\!\!Q$; and

Q is H, lower alkyl or $-\!\!-\!\!N(R_1)(R_2)$;

$R_1$, $R_2$ and $R_3$ are H, lower alkyl, alkylene carboxylate, alkylene phosphonate or alkylene sulfonate, or 2-ethyl-3-N-vinyl pyrrolidonyl;

$R_3$ is H and $R_1$ and/or $R_2$ is

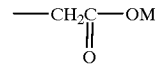

where M is H or monovalent alkali metal;

X is alkylene, arylene, cycloalkylene or a heterocylic metal chelating group, and n is 1–10.

2. A monomer of claim 1 in which

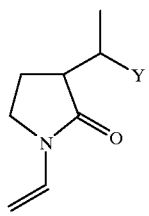 where Y is —N(R₃)—(X)ₙ—Q ; and

Q is H, lower alkyl or —N(R₁)(R₂) ;

R₁, R₂ and R₃ are H, lower alkyl, alkylene carboxylate or 2-ethyl-3-N-vinyl pyrrolidonyl;
X is alkylene, arylene, cycloalkylene or a heterocylic metal chelating group and n is 1–6.

3. A monomer of claim 1 in which Q is

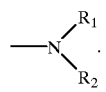

4. A monomer of claim 1 in which Q is H.
5. A monomer of claim 1 in which Q is lower alkyl.
6. A monomer of claim 1 in which n is 1–6.
7. A monomer of claim 3 in which R₃ is H.
8. A monomer of claim 3 in which R₁ and/or R₂ is alkylene carboxylate.
9. A monomer of claim 3 in which R₁, R₂ and R₃ are H, X is —CH₂ and n is 2.
10. A monomer according to claim 1 in which Y is selected from the group consisting of

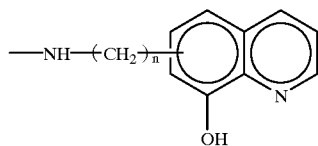

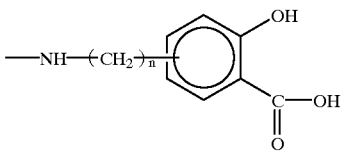

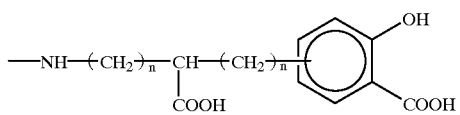

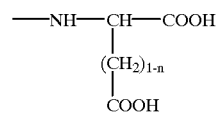

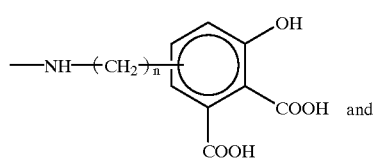

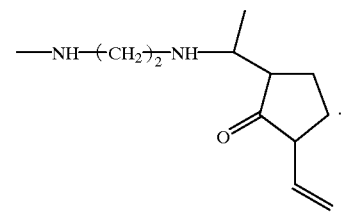

11. A monomer according to claim 1 which is 3-(2-aminoethyl)-α-aminoethyl-N-vinyl pyrrolidone, AEAEVP, having the formula:

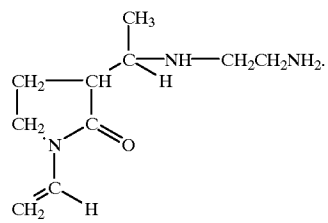

12. A process of making the monomer of claim 1 which comprises reacting 1-vinyl-3-(E)-ethylidene pyrrolidone, EVP, with ethylenediamine, EDA, under Michael addition conditions.
13. A process according to claim 12 wherein the reaction is carried out in the absence of a solvent.
14. A process according to claim 13 wherein an excess of EDA is used over a 1:1 ratio of reactant.
15. A process according to claim 13 which is carried out under pressure at about 100° C.
16. A process according to claim 13 wherein the excess EDA is stripped off after the Michael addition reaction.

* * * * *